US00PP19354P2

(12) United States Plant Patent
Tas

(10) Patent No.: US PP19,354 P2
(45) Date of Patent: Oct. 21, 2008

(54) ***ALSTROEMERIA* PLANT NAMED 'TESROBIN'**

(50) Latin Name: *Alstroemeria hybrida*
Varietal Denomination: Tesrobin

(75) Inventor: Marius Jan Tas, CA De Kwakel (NL)

(73) Assignee: VOF Hortipartners, Heerhugowaard (NL)

( * ) Notice: Subject to any disclaimer, the term of this patent is extended or adjusted under 35 U.S.C. 154(b) by 0 days.

(21) Appl. No.: 11/978,491

(22) Filed: Oct. 29, 2007

(51) Int. Cl.
*A01H 5/00* (2006.01)

(52) U.S. Cl. ..... Plt./309

(58) Field of Classification Search ..... Plt./309
See application file for complete search history.

(56) References Cited

PUBLICATIONS

GTITM UPOVROM Citation for 'Tesrobin' as per QZ PBR 20052400; filed Nov. 23, 2005.*

* cited by examiner

*Primary Examiner*—Kent L Bell
(74) *Attorney, Agent, or Firm*—C. A. Whealy

(57) ABSTRACT

A new and distinct cultivar of *Alstroemeria* plant named 'Tesrobin', characterized by its compact and mounding plant habit; sturdy and strong plants; vigorous growth habit; intense red-colored flowers; and good garden performance.

1 Drawing Sheet

Botanical designation: *Alstroemeria hybrida.*
Cultivar denomination: 'Tesrobin'.

BACKGROUND OF THE INVENTION

The present invention relates to a new and distinct cultivar of *Alstroemeria* plant, botanically known as *Alstroemeria hybrida,* grown typically as a potted garden *Alstroemeria,* and hereinafter referred to by the name 'Tesrobin'.

The new *Alstroemeria* is a product of a planned breeding program conducted by the Inventor in De Kwakel, The Netherlands. The objective of the breeding program is to create new potted garden *Alstroemeria* cultivars that flower continuously and have attractive foliage and flower coloration.

The new *Alstroemeria* originated from a cross-pollination made by the Inventor in De Kwakel, The Netherlands in May, 2003, of a proprietary *Alstroemeria hybrida* selection identified as code number E607, not patented, as the female, or seed, parent with a proprietary *Alstroemeria hybrida* selection identified as code number ZB4061A, not patented, as the male, or pollen, parent. The cultivar Tesrobin was discovered and selected by the Inventor as a flowering plant from within the progeny of the stated cross-pollination in a controlled environment in De Kwakel, The Netherlands in May, 2004.

Asexual reproduction of the new *Alstroemeria* by root divisions in a controlled environment in De Kwakel, The Netherlands since the fall of 2004, has shown that the unique features of this new *Alstroemeria* are stable and reproduced true to type in successive generations.

SUMMARY OF THE INVENTION

The cultivar Tesrobin has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Tesrobin'.

These characteristics in combination distinguish 'Tesrobin' as a new and distinct cultivar of *Alstroemeria:*

1. Compact and mounding plant habit.
2. Sturdy and strong plants; vigorous growth habit.
3. Intense red-colored flowers.
4. Good garden performance.

Plants of the new *Alstroemeria* can be compared to plants of the parent selections. Plants of the new *Alstroemeria* differ from plants of the parent selections primarily in flower color as plants of the parent selections have pink-colored flowers.

Plants of the new *Alstroemeria* can be compared to plants of the *Alstroemeria hybrida* cultivar Staprivane, disclosed in U.S. Plant Pat. No. 14,131. Plants of the new *Alstroemeria* differ primarily from plants of the cultivar Staprivane in flower color as plants of the cultivar Staprivane have purple-colored flowers. In addition, plants of the new *Alstroemeria* have shorter peduncles than plants of the cultivar Staprivane.

Plants of the new *Alstroemeria* can also be compared to plants of the *Alstroemeria hybrida* cultivar Staprioxa, disclosed in U.S. Plant Pat. No. 14,075. Plants of the new *Alstroemeria* differ primarily from plants of the cultivar Staprioxa in flower color as plants of the cultivar Staprioxa have red purple and yellow-colored flowers. In addition, plants of the new *Alstroemeria* have shorter and stronger peduncles than plants of the cultivar Staprioxa.

BRIEF DESCRIPTION OF THE PHOTOGRAPH

The accompanying colored photograph illustrates the overall appearance of the new *Alstroemeria,* showing the colors as true as it is reasonably possible to obtain in colored reproductions of this type. Colors in the photograph may differ slightly from the color values cited in the detailed botanical description which accurately describe the colors of the new *Alstroemeria.* The photograph comprises a side perspective view of a typical flowering plant of 'Tesrobin' grown in a container.

DETAILED BOTANICAL DESCRIPTION

The aforementioned photograph and following observations and measurements describe plants of the new *Alstroemeria* grown in De Kwakel, The Netherlands during the winter in a glass-covered greenhouse in containers. During the production of the plants, day temperatures averaged 20° C. and night temperatures averaged 14° C. Plants used for the photograph and description were about ten weeks from planting. Color references are made to The Royal Horticultural Society Colour Chart, 1995 Edition, except where general terms of ordinary dictionary significance are used.

Botanical classification: *Alstroemeria hybrida* cultivar Tesrobin.

Parentage:

*Female, or seed, parent.*—Proprietary *Alstroemeria hybrida* selection identified as code number E607, not patented.

*Male or pollen parent.*—Proprietary *Alstroemeria hybrida* selection identified as code number ZB4061A, not patented.

Propagation:

*Type.*—By root divisions.

*Time to produce a rooted young plant, summer.*—About 49 days at 20° C.

*Time to produce a rooted young plant, winter.*—About 56 days at 16° C.

*Root description.*—Fibrous, fleshy; up to 2 cm in thickness; color, close to 155D.

*Rooting habit.*—Freely branching; moderately dense.

*Rhizomes.*—Shape: Elongate; rounded. Length: About 5 cm. Diameter: About 8 mm. Texture: Smooth. Color: Close to 157D.

Plant description:

*Plant habit.*—Compact and mounded; freely branching, bushy appearance. Sturdy and strong plants; vigorous growth habit.

*Plant height.*—About 20 cm.

*Plant diameter* (*area of spread*).—About 35 cm.

Stem description:

*Aspect.*—Mostly upright to somewhat outwardly spreading.

*Internode length.*—About 1.5 cm.

*Strength.*—Strong.

*Texture.*—Smooth, glabrous.

*Color.*—Close to 137C.

Foliage description:

*Arrangement.*—Alternate; below the peduncles in a single whorl; sessile.

*Length.*—About 9 cm.

*Width.*—About 3.3 cm.

*Shape.*—Obovate.

*Apex.*—Acute.

*Base.*—Attenuate.

*Margin.*—Entire.

*Texture, upper and lower surfaces.*—Smooth, glabrous.

*Venation pattern.*—Parallel.

*Color.*—Developing and fully developed foliage, upper surface: Close to 147A; venation, close to 147A. Developing and fully developed foliage, lower surface: Close to 137A; venation, close to 137A.

Flower description:

*Flower type and habit.*—Single cup-shaped flowers arranged in compound umbels. Flowers face upright or outwardly. Perianth segments separate. Freely flowering habit; about 50 flowers develop per plant.

*Natural flowering season.*—Flowering continuous from the spring until frost in The Netherlands.

*Fragrance.*—None detected.

*Flower longevity on the plant.*—About one to two weeks; flowers not persistent.

*Flower buds* (*showing color*).—Length: About 4.5 cm. Diameter: About 1.6 cm. Shape: Roughly ovoid. Color: Close to 53A; towards the apex, close to 137A.

*Umbel height.*—About 10 cm.

*Umbel diameter.*—About 13 cm.

*Flower diameter.*—About 5.5 cm.

*Flower depth* (*height*).—About 5.5 cm.

*Perianth.*—Arrangement: Six arranged in two whorls, each whorl with two lateral and one median segments. Size, inner perianth: Length, lateral segments: About 5.5 cm. Width, lateral segments: About 1.6 cm. Length, median segment: About 5 cm. Width, median segment: About 1.7 cm. Size, outer perianth: Length, lateral segments: About 5.5 cm. Width, lateral segments: About 2.5 cm. Length, median segment: About 5 cm. Width, median segment: About 2.5 cm. Shape, inner perianth, lateral and median segments: Obovate. Shape, outer perianth, lateral and median segments: Obovate. Apex, inner perianth, lateral and median segments: Mucronate. Apex, outer perianth, lateral and median segments: Embedded point. Base, inner and outer perianths, lateral and median segments: Attenuate. Margin, inner and outer perianths, lateral and median segments: Entire. Texture, inner and outer perianths, lateral and median segments: Smooth, glabrous. Color, inner perianth: When opening and fully opened, lateral segments, upper surface: Close to 53C; color becoming closer to 53D with development; stripes, close to 187A. When opening and fully opened, median segment, upper surface: Close to 53C; color becoming closer to 53D with development. When opening and fully opened, lateral segments, lower surface: Close to 50C; stripes, close to 187A. When opening and fully opened, median segment, lower surface: Close to 53D. Color, outer perianth: When opening and fully opened, lateral and median segments, upper surface: Close to 53C; color becoming closer to 53D with development. When opening and fully opened, lateral and median segments, lower surface: Close to 53C.

*Peduncles.*—Length: About 2.5 cm. Diameter: About 3 mm. Strength: Strong. Angle: Erect to about 30° C. from vertical. Texture: Smooth, glabrous. Color: Close to 137C.

*Reproductive organs.*—Stamens: Quantity per flower: Six. Anther shape: Elliptical. Anther length: Less than 1 cm. Anther color: Close to 152C. Pollen amount: Abundant. Pollen color: Close to 148C. Pistils: Quantity per flower: One. Style length: About 4.5 cm. Style color: Towards the apex, close to 53C; towards the base, close to 51B. Stigma color: Close to 53C. Ovary color: Close to 137C.

*Fruit/seed.*—Fruit and seed development has not been observed.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind, rain and temperatures ranging from about 1° C. to about 35° C.

It is claimed:

1. A new and distinct *Alstroemeria* plant named 'Tesrobin' as illustrated and described.

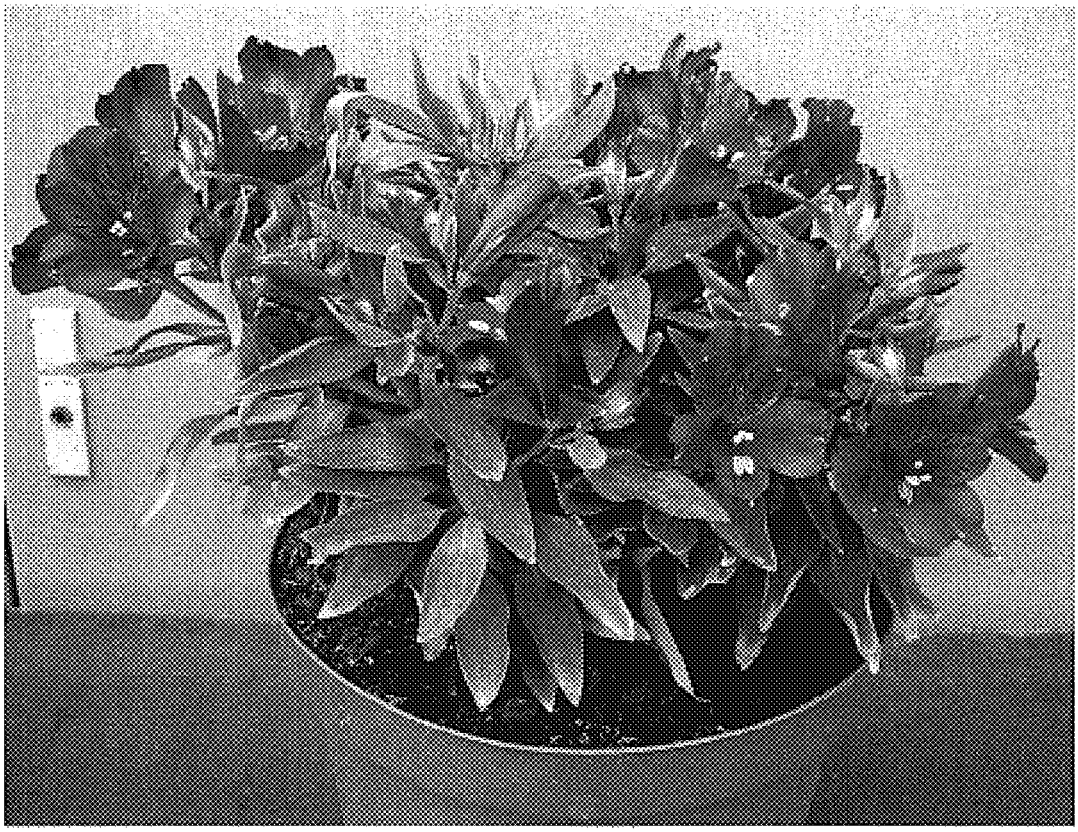

* * * * *